United States Patent [19]

Albright, Jr.

[11] Patent Number: 5,347,052
[45] Date of Patent: Sep. 13, 1994

[54] PREPARATION OF 3,5-DIAMINOBENZOTRIFLUORIDE

[75] Inventor: David E. Albright, Jr., Niagara Falls, N.Y.

[73] Assignee: Occidental Chemical Corporation, Niagara Falls, N.Y.

[21] Appl. No.: 685,106

[22] Filed: Apr. 15, 1991

[51] Int. Cl.$^5$ .......................... C07C 209/32
[52] U.S. Cl. .................... 564/417; 564/415; 564/416; 564/422; 564/423
[58] Field of Search .............. 564/417, 423, 415, 422

[56] References Cited

U.S. PATENT DOCUMENTS 3,073,865  1/1963  Spiegler .................. 564/417

FOREIGN PATENT DOCUMENTS 38465  10/1981  European Pat. Off. .......... 564/417

OTHER PUBLICATIONS

Paal et al, Ber. 64 B, 2142–50, 1931.

Primary Examiner—Shailendra Kumar
Attorney, Agent, or Firm—Wayne A. Jones; Richard D. Fuerle

[57] ABSTRACT

3,5-Diaminobenzotrifluoride can be produced, in a single step, by reacting 4-chloro-3,5-dinitrobenzotrifluoride, in methanol, with hydrogen gas, in the presence of magnesium oxide, and in the presence of a catalyst comprising palladium on a carbon support.

20 Claims, No Drawings

PREPARATION OF 3,5-DIAMINOBENZOTRIFLUORIDE

BACKGROUND OF THE INVENTION

This invention relates to a process for the preparation of 3,5-diaminobenzotrifluoride by the reduction of 4-chloro-3,5-dinitrobenzotrifluoride using hydrogen as a reducing agent in the presence of palladium on carbon as a catalyst. Since 4-chloro-3,5-diaminobenzotrifluoride is difficult to separate from 3,5-diaminobenzotrifluoride itself, it is a particular object of the present invention to provide a process which produces 3,5-diaminobenzotrifluoride without significant production of 4-chloro-3,5-diaminobenzotrifluoride.

The reduction of aromatic nitro compounds containing halogen on the aromatic ring is unpredictable. Hydrogenation using a palladium on carbon catalyst generally reduces the nitro group to an amine. However, the hydrogenation has been reported to fail in some cases. In addition, the effects of such hydrogenation upon a ring halogen are unpredictable. Occasionally the ring halogen is removed from the ring and replaced by a hydrogen. However, in many cases the hydrogenation leaves the ring halogen intact.

A. Weizmann discloses in J. Am. Chem. Soc., 71, 4154 (1949), that the catalytic hydrogenation of diethyl aminoethyl 4-nitro-2-chlorobenzoate using palladium on barium sulfate as a catalyst was impractical from a preparative point of view. The nitro compound was often incompletely reduced. The chlorine was occasionally removed from the ring while in other reactions it remained on the ring. Similar hydrogenation experiments conducted with 4-nitro-2-chlorobenzoic acid and its ethyl ester, using palladium on barium sulfate as a catalyst, produced variable results depending upon the solvent employed. In ethyl acetate, the reduction proceeded with retention of the chlorine. In this solvent, the acid and the ethyl ester gave quantitative yields of 4-amino-2-chlorobenzoic acid and ethyl 4-amino-2-chlorobenzoate, respectively. In isopropyl alcohol, the 4-nitro-2-chlorobenzoic acid and its ethyl ester were reduced to 4-aminobenzoic acid and its ethyl ester, respectively. In other words, in isopropyl alcohol the chlorine was removed in the reduction process. An aqueous solution of sodium 4-nitro-2-chlorobenzoate yielded, on workup, 4-aminobenzoic acid.

Bouchet et al. disclose in Syn. Commun., 4, 57–9 (1974), as cited in CA 81:25598m, that paranitrochlorobenzene may be reduced to parachloroaniline using hydrogen in the presence of a palladium on carbon catalyst in an aqueous alcohol solvent buffered to pH 7.

Ovchinnikov et al. (in Prikl. Hkim., (62), 37–44 (1969)) disclosed that meta and para chloronitrobenzenes may be hydrogenated to meta and parachloroanilines, respectively, using hydrogen gas and a 2% palladium on carbon catalyst. Approximately 2% dehalogenation was observed. It was also observed that the amount of dehalogenation was related to the type of carbon used as the catalyst carrier and depended upon the height of the catalyst bed.

U.S. Pat. No. 3,566,813 discloses that aromatic haloamines can be prepared by hydrogenating the corresponding chloro-nitro aromatic compound in the presence of a modified palladium on charcoal catalyst. The palladium on carbon catalyst is modified by treating it with a solution of a bismuth, lead, or silver salt.

U.S. Pat. No. 3,073,865 discloses a process for catalytically reducing halogen-substituted aromatic nitro compounds to the corresponding amines. The process is designed to reduce the aromatic nitro compound without removing the ring-halogens. The inventor discloses that magnesium oxide at levels between 0.1 and 1% by weight of nitro compound being reduced tends to prevent dehalogenation. At higher levels of magnesium oxide, magnesium oxide tends to promote dehalogenation. However, the examples provided in the patent show that in cases where the process did not produce the desired retention of the halogen atom, dehalogenation occurred to the extent of approximately 40%. In one case, a dechlorination of 80% occurred.

C. Paal and Christian Muller-Lobeck, Ber. 64b 2142–50 (1931), (as cited in CA 26 pp. 85 and 86) studied the hydrogenation of α and β-chloro butyric acid, α and β-chloro proprionic acid, and α and β-chloro ethyl benzene. In each case, the α-chloro molecule more readily reacts with hydrogen to remove the chlorine than does the β-chloro isomer. The catalyst employed for the reaction was palladium. The authors also observed that magnesium oxide promoted the reaction by reacting with the HCl released. In the absence of a base to absorb the HCl, the liberated acid prevents further hydrogenation.

European Patent Application EP 88667 (as abstracted in Chem. Abstracts 100:52475m and Derwent accession #C83-089930) discloses that chlorinated or brominated methylenedianilines can be prepared by the nitration and reduction of the corresponding aromatic halides. The reduction is carried out in methanol solvent with hydrogen gas in the presence of 5% palladium on carbon as a catalyst. The aromatic halide is retained during reduction.

Chakrabarti et al. disclose in two papers (J. Med. Chem. 23 pp. 878 and 884 (1980)) a multi-step reduction and cyclization reaction in which the first step is a hydrogenation using 10% palladium on carbon as a catalyst. The solvent was a mixture of ethanol and ethyl acetate. The molecules that are subjected to hydrogenation are substituted nitrobenzenes with a halogen at the 3 position and a substituted amino group at the 6 position. In one paper, the compound studied has fluorine as the halogen and in the other the halogen is chlorine. In each case, the nitro group was reduced to the amine while the halogen was not attacked.

Japanese Patent 63/010739 (as abstracted in Chem. Abstracts 109:92449y) discloses that chloro-fluoro-benzotrifluoride derivatives can be dechlorinated using hydrogen gas and 5% palladium charcoal catalysts in a methanol solvent. The ring chlorines are preferentially removed over the ring fluorines. Apparently no base was used in this process. Comparative Example 9 illustrates that a base is required to reduce the compound of the Applicant's process.

Vergnani et al. disclosed in Helv. Chim. Acta, 68, 1828, (1985), that 5-bromo-2-methyl-8-nitro-1,2,3,4-tetrahydroisoquinoline undergoes simultaneous removal of the aromatic bromine and reduction of the nitro group to an amine when treated with hydrogen gas in the presence of a 10% palladium on charcoal catalyst and triethylamine using methanol as a solvent.

Japanese Patent 58157749 (as abstracted in Chem. Abstracts 100:51247b) discloses that 2,2',4-trichloro-4',5-dinitrodiphenyl ether may be hydrogenated in the presence of 5% palladium on carbon catalyst in methanol to form 3,4'-diaminodiphenyl ether.

The substance that is reduced using the process of this invention, that is, 4-chloro-3,5-dinitrobenzotrifluoride, is a rather reactive molecule and can undergo side reactions during any reduction process. Crampton and Greenhalgh have disclosed in J. Chem. Soc., Perkins Transaction II, p. 187 (1986), that 4-chloro-3,5-dinitrobenzotrifluoride is subject to nucleophyllic attack on the chlorine. Thus, hydroxide ion can displace the chlorine to yield 4-hydroxy-3,5-dinitrobenzotrifluoride.

European Patent 038,465 discloses the reduction of 2-trifluoromethyl-4-chloronitrobenzene to 2-trifluoromethylaniline in a single step using hydrogen gas in a polar medium. The preferred solvent is water and/or a 1-3 carbon alcohol, especially methanol, and the preferred bases are alkali hydroxides, ammonia, or lower aliphatic amines. Attempts were made in our laboratory to reduce 4-chloro-3,5-dinitrobenzotrifluoride using the method set forth in European Patent 038,465. Comparative Example 1 and 2 illustrate that the procedure of this patent does not work in the case of 4-chloro-3,5-dinitrobenzotrifluoride. If the sodium hydroxide is added as part of the initial charge, the level of impurities is extremely high. On the other hand, if the nitro groups are reduced, and then the sodium hydroxide is added, the impurity level is only 6.3%. However, the amount of 4-chloro-3,5-diaminobenzotrifluoride found is approximately 40%.

SUMMARY OF THE INVENTION

Surprisingly, we have now found that 3,5-diaminobenzotrifluoride can be produced, in a single step, by reacting 4-chloro-3,5-dinitrobenzotrifluoride, in methanol, with hydrogen gas and magnesium oxide, in the presence of a catalyst comprising palladium on a carbon support. 3,5-Diaminobenzotrifluoride is a valuable intermediate used in the synthesis of polyimide polymers. The present process is advantageous in that the starting material, 4-chloro-3,5-dinitrobenzotrifluoride is commercially available.

DETAILED DESCRIPTION OF THE INVENTION

It is an object of the present invention to provide a process that produces 3,5-diaminobenzotrifluoride containing a very low level of impurities and particularly very little, if any, 4-chloro-3,5-diaminobenzotrifluoride. It is desirable that the final product contain no more than 0.5% of the 4-chloro-3,5-diaminobenzotrifluoride side product. 4-Chloro-3,5-diaminobenzotrifluoride is a particularly troublesome impurity since it is very difficult to separate from the desired 3,5-diaminobenzotrifluoride. The vapor pressure difference between 4-chloro-3,5-diaminobenzotrifluoride and 3,5-diaminobenzotrifluoride is small, and therefore, separation by distillation is difficult. In addition, the chloro compound appears to be more volatile than the diamino compound itself, and accordingly, any attempt to distill crude 3,5-diaminobenzotrifluoride containing a small percentage of 4-chloro-3,5-diaminobenzotrifluoride produces a distillate richer in the 4-chloro product. Other processes that might be used include multi-step recrystallizations and multiple extraction. These latter two processes are expensive and therefore not preferred.

It is a further object of the proposed invention to conduct the reaction in a solvent, such as methanol, that may be readily removed from the reaction mixture, and easily recycled. In addition, a solvent such as methanol will tend to keep water in solution rather than allowing it to separate. There are many advantages to having the reaction conducted in a homogeneous phase, rather than in a two-phase system.

3,5-Diaminobenzotrifluoride can be produced, in a single step, by reacting 4-chloro-3,5-dinitrobenzotrifluoride in methanol, with hydrogen gas and magnesium oxide, in the presence of a catalyst comprising palladium on a carbon support. It is also preferable to handle the catalyst wet. The preferred form for the catalyst is 2 to 10% on a carbon support. The most preferred catalyst is 5% palladium on carbon. A particular advantage of using a palladium on carbon catalyst is that the palladium can be easily recovered when the catalyst loses effectiveness.

While the reaction can be conducted with widely varying amounts of catalyst, obviously, the reaction tends to be slow if insufficient catalyst is used. For the preferred catalyst (5% Pd on carbon), the reaction can be run at a wide range of catalyst levels. Concentration as low as about 0.5 g of catalyst (dry weight) per 100 g of 4-chloro-3,5-dinitrobenzotrifluoride can be used. The preferred range is 4 to 6 g of catalyst (dry weight) per 100 g of 4-chloro-3,5-dinitrobenzotrifluoride.

The magnesium oxide base not only serves to speed up the reaction, but, as will be set forth more fully below, influences the actual course of the reaction. Although we do not wish to be bound by theory, it is possible that a base speeds up the reaction by reacting with the hydrogen chloride formed when the chlorine is removed from the ring by attack of the hydrogen. In the absence of a base, the hydrogen chloride produced tends to poison the palladium catalyst. This diminishes the activity of the catalyst, and leads to incomplete conversion of starting material to product.

As shown in the Comparative Examples, the use of bases other than magnesium oxide leads to side reactions when methanol is the solvent. As set forth below, methanol is an advantageous solvent for this reaction. Thus, it is an advantage of magnesium oxide as a base that one can conduct the reaction in methanol. The use of methanol is advantageous since it has a rather low boiling point and can be readily removed when the reaction is completed. In addition, methanol can be readily recycled because it does not form an azeotrope with water and thus, can be separated from the water produced in the reaction by distillation.

The reaction is conducted at moderate pressure; that is, about 30 to 75 psig. At the lower end, the pressure is not critical. Although the reaction can be run at pressures less than 30 psig, such reactions tend to be slow. Accordingly, it is preferred to run the reaction at about 40 psig. A total pressure of 75 psig is not an upper limit on the useable pressure, but is rather the upper end of the preferred range of operation. To speed the rate of hydrodechlorination, the reaction should be run up to about 300 psig. The hydrogen pressure can be approximated by subtracting the known vapor pressure of methanol from the total pressure.

The reaction can be conducted at moderate temperatures between room temperature and about 125° C. If the reaction is run at a temperature much lower than room temperature, it tends to be too slow to be useful. In practice, we have found it convenient to mix the reactants at about room temperature and allow the heat of the reaction to warm the reaction mixture to a temperature of about 80°-90° C. The temperature can be controlled by slowing down the feed rate of hydrogen.

After the initial phase of the reaction, the temperature is held at about 80°–90° C. for a period of one to two hours. In larger reactors, depending upon the nature of the heat exchange available, a slower rate of hydrogen addition may be required to keep the temperature in the range of about 80°–90° C. In such cases the reaction will take somewhat longer. It is important to watch the temperature carefully since methanol has an appreciable vapor pressure at temperatures above 125° C. and this added pressure can create problems.

The preferred method for isolating and purifying 3,5-diaminobenzotrifluoride is solvent evaporation followed by distillation. Methods such as recrystallization and other methods well-known to those skilled in the art can be used, but are not preferred.

EXAMPLES

Example 1

A solution of 4-chloro-3,5-dinitrobenzotrifluoride (10 g) in methanol (100 mL) was charged in a Parr hydrogenator bottle and mixed with magnesium oxide (1.6 g—two equivalents based upon 4-chloro-3,5-dinitrobenzotrifluoride) and with a carbon supported palladium catalyst (5% Pd on carbon containing 50% water, 1.2 g wet weight). After purging with nitrogen, hydrogen was charged periodically in the reaction bottle to maintain its pressure at 40–50 psig. The reaction temperature began at approximately 20° C. and began to rise as soon as the agitation began. In eight minutes, the temperature rose to 87° C. and was held at 80° C. for 1.5 hours. The reaction mixture was then allowed to cool to room temperature over approximately 42 minutes. After the reaction, analysis of the reaction mixture by gas chromatography showed formation of 6.29 g of 3,5-diaminobenzotrifluoride and no 4-chloro-3,5-diaminobenzotrifluoride was detectable. The yield of 3,5-diaminobenzotrifluoride was 97% based upon starting material.

Example 2

A solution of 4-chloro-3,5-dinitrobenzotrifluoride (10 g) in methanol (100 mL) was charged in a Parr hydrogenator bottle and mixed with magnesium oxide (3.0 g—four equivalents based upon 4-chloro-3,5-dinitrobenzotrifluoride) and with a carbon supported palladium catalyst (5% Pd on carbon containing 50% water, 1.2 g wet weight). After purging with nitrogen, hydrogen was charged periodically in the reaction bottle to maintain its pressure at 40–50 psig. The reaction began at 20° C. and began to rise as soon as agitation began. The temperature rose to 72° C. in fourteen minutes. The reaction mixture was held at 75° C. for twenty-two minutes and then allowed to cool to room temperature over a period of 28 minutes. After the reaction, analysis of the reaction mixture by gas chromatography showed formation of 6.1 g of 3,5-diaminobenzotrifluoride and 0.28 g of 4-chloro-3,5-diaminobenzotrifluoride. The yield of 3,5-diaminobenzotrifluoride was 94% based upon starting material.

Example 3

A solution of 4-chloro-3,5-dinitrobenzotrifluoride (20 g) in methanol (200 mL) was charged in a Parr hydrogenator bottle and mixed with magnesium oxide (3.2 g—two equivalents based upon 4-chloro-3,5-dinitrobenzotrifluoride) and with a carbon supported palladium catalyst (5% Pd on carbon containing 50% water, 1.2 g wet weight). After purging with nitrogen, hydrogen was charged periodically in the reaction bottle to maintain its pressure at 40–50 psig. The reaction temperature began at approximately 19° C. and began to rise as soon as the agitation began. In eighteen minutes, the temperature rose to 94° C. and was held at 80° C. for 2 hours. The reaction mixture was then allowed to cool to room temperature over approximately 85 minutes. After the reaction, analysis of the reaction mixture by gas chromatography showed formation of 12.9 g of 3,5-diaminobenzotrifluoride and 0.06 g of 4-chloro-3,5-diaminobenzotrifluoride. The yield of 3,5-diaminobenzotrifluoride was 99% based upon starting material.

Example 4

A solution of 4-chloro-3,5-dinitrobenzotrifluoride (10 g) in methanol (100 mL) was charged in a Parr hydrogenator bottle and mixed with magnesium oxide (0.8 g—one equivalent based upon 4-chloro-3,5-dinitrobenzotrifluoride) and with a carbon supported palladium catalyst (5% Pd on carbon containing 50% water, 1.2 g wet weight). After purging with nitrogen, hydrogen was charged periodically in the reaction bottle to maintain its pressure at 40–50 psig. The reaction temperature began at approximately 20° C. and began to rise as soon as the agitation began. In seven minutes, the temperature rose to 84° C. and was held at 80° C. for 73 minutes. The reaction mixture was then allowed to cool to room temperature over approximately 30 minutes. After the reaction, analysis of the reaction mixture by gas chromatography showed formation of 5.81 g of 3,5-diaminobenzotrifluoride and 0.04 g of 4-chloro-3,5-diaminobenzotrifluoride. The yield of 3,5-diaminobenzotrifluoride was 89% based upon starting material.

Example 5

A solution of 4-chloro-3,5-dinitrobenzotrifluoride (10 g) in methanol (60 mL) was charged in a Parr hydrogenator bottle and mixed with magnesium oxide (1.6 g—two equivalents based upon 4-chloro-3,5-dinitrobenzotrifluoride) and with a carbon supported palladium catalyst (5% Pd on carbon containing 50% water, 1.2 g wet weight). After purging with nitrogen, hydrogen was charged periodically in the reaction bottle to maintain its pressure at 40–50 psig. The reaction temperature began at approximately 22° C. and began to rise as soon as the agitation began. In thirteen minutes, the temperature rose to 80° C. and was held at 80° C. for 1.5 hours. The reaction mixture was then allowed to cool to room temperature and removed in approximately 108 minutes. After the reaction, analysis of the reaction mixture by gas chromatography showed formation of 5.65 g of 3,5-diaminobenzotrifluoride and 0.08 g of 4-chloro-3,5-diaminobenzotrifluoride. The yield of 3,5-diaminobenzotrifluoride was 87% based upon starting material.

Example 6

A solution of 4-chloro-3,5-dinitrobenzotrifluoride (10 g) in methanol (60 mL) was charged in a Parr hydrogenator bottle and mixed with magnesium oxide (1.6 g—two equivalents based upon 4-chloro-3,5-dinitrobenzotrifluoride) and with a carbon supported palladium catalyst (5% Pd on carbon containing 50% water, 0.8 g wet weight). After purging with nitrogen, hydrogen was charged periodically in the reaction bottle to maintain its pressure at 40–50 psig. The reaction temperature began at approximately 20° C. and began to rise as soon as the agitation began. In six minutes, the temperature rose to 80° C. and was held at 80° C. for 1 hours. The reaction mixture was then allowed to cool to room temperature over approximately 30 minutes. After the reaction, analysis of the reaction mixture by gas chromatography showed formation of 5.84 g of 3,5-diaminobenzotrifluoride and 0.48 g of 4-chloro-3,5-diaminobenzotrifluoride. The yield of 3,5-diaminobenzotrifluoride was 90% based upon starting material.

Example 7

A solution of 4-chloro-3,5-dinitrobenzotrifluoride (10 g) in methanol (100 mL) was charged in a Parr hydrogenator bottle and mixed with magnesium oxide (1.6 g—two equivalents based upon 4-chloro-3,5-dinitrobenzotrifluoride) and with a carbon supported palladium catalyst (5% Pd on carbon containing 50% water, 0.8 g wet weight). After purging with nitrogen, hydrogen was charged periodically in the reaction bottle to maintain its pressure at 40-50 psig. The reaction temperature began at approximately 20° C. and began to rise as soon as the agitation began. In ten minutes, the temperature rose to 83° C. and was held at 80° C. for 105 minutes. The reaction mixture was then allowed to cool to room temperature over approximately 32 minutes. After the reaction, analysis of the reaction mixture by gas chromatography showed formation of 6.23 g of 3,5-diaminobenzotrifluoride and 0.03 g of 4-chloro-3,5-diaminobenzotrifluoride. The yield of 3,5-diaminobenzotrifluoride was 96% based upon starting material.

Comparative Example 1

A solution of 10 g of 4-chloro-3,5-dinitrobenzotrifluoride in methanol (100 mL) was charged in a Parr hydrogenator bottle and mixed with 1.2 g of carbon supported palladium catalyst (5% Pd on carbon—50% wet) and 1.5 g of sodium hydroxide. After purging with nitrogen, hydrogen was charged periodically in the reaction bottle to maintain its pressure at 40-50 psig. The reaction temperature began at approximately 24° C. and began to rise as soon as the agitation began. In twenty-nine minutes, the temperature rose to 79° C. and was held at 80° C. for 24 minutes. The reaction mixture was then allowed to cool to room temperature over approximately 20 minutes. After the reaction, the analysis of the mixture by gas chromatography showed the formation of 1.19 g of 3,5-diaminobenzotrifluoride, and 0.113 g of 4-chloro-3,5-diaminobenzotrifluoride. The yield of 3,5-diaminobenzotrifluoride was 31% based upon starting material.

Comparative Example 2

A solution of 10 g of 4-chloro-3,5-dinitrobenzotrifluoride in methanol (100 mL) was charged in a Parr hydrogenator bottle and mixed with 1.2 g of carbon supported palladium catalyst (5% Pd on carbon—50% wet). After purging with nitrogen, hydrogen was charged periodically in the reaction bottle to maintain its pressure at 40-50 psig. The reaction temperature began at approximately 19° C. and began to rise as soon as the agitation began. In six minutes, the temperature rose to 76° C. The reaction mixture was then allowed to cool to 42° C. over approximately 20 minutes. At this point, 1.5 g of sodium hydroxide in 30 mL of methanol was added and hydrogenation was continued. During this phase of hydrogenation, the reaction mixture was warmed from 42° to 80° C. in thirty-four minutes, and then allowed to cool from 80° C. to room temperature in a period of thirty minutes. After the reaction, the analysis of the mixture by gas chromatography showed the presence of 3.62 g of 3,5-diaminobenzotrifluoride, and 2.45 g of 4-chloro-3,5-diaminobenzotrifluoride. The yield of 3,5-diaminobenzotrifluoride was 56% based upon starting material.

Comparative Example 3

A solution of 10 g of 4-chloro-3,5-dinitrobenzotrifluoride in methanol (100 mL) was charged in a Parr hydrogenator bottle and mixed with a carbon supported palladium catalyst (5% Pd on carbon containing 50% water (1.2 g)), and 2.1 g of calcium oxide. After purging with nitrogen, hydrogen was charged periodically in the reaction bottle to maintain its pressure at 40-50 psig. The reaction temperature began at approximately 22° C. and began to rise as soon as the agitation began. In fourteen minutes, the temperature rose to 75° C. and was held at 80° C. for 47 minutes. The reaction mixture was then allowed to cool to room temperature over approximately 40 minutes. After the reaction, the analysis of the mixture by gas chromatography showed the presence of 0.90 g of 3,5-diaminobenzotrifluoride and 0.86 g of 4-chloro-3,5-diaminobenzotrifluoride. The yield of 3,5-diaminobenzotrifluoride was 14% based upon starting material.

Comparative Example 4

A solution of 5 g of 4-chloro-3,5-dinitrobenzotrifluoride in methanol (70 mL) was charged in a Parr hydrogenator bottle and mixed with a carbon supported palladium catalyst (5% Pd on carbon containing 50% water, 0.6 g), and 2.0 g of sodium carbonate (2 equivalents based upon the 4-chloro-3,5-dinitrobenzotrifluoride). After purging with nitrogen, hydrogen was charged periodically in the reaction bottle to maintain its pressure at 40-50 psig. The reaction mixture started at about 20° C. and was warmed, in ten minutes, to 80° C. both by the heat of reaction, and by external heat application. The temperature was maintained at 80° C. for about an hour. The reaction was then allowed to cool to room temperature over a period of 30 minutes. After the reaction, the analysis of the mixture by gas chromatography showed the presence of 2.04 g of 3,5-diaminobenzotrifluoride and 0.072 g of 4-chloro-3,5-diaminobenzotrifluoride. The yield of 3,5-diaminobenzotrifluoride was 63% based upon starting material. In addition, a substantial percentage of starting material was not accounted for and apparently formed products not detected by gas chromatography.

Comparative Example 5

A solution of 10 g of 4-chloro-3,5-dinitrobenzotrifluoride in ethanol (100 mL) was charged in a Parr hydrogenator bottle and mixed with a carbon supported palladium catalyst (5% Pd on carbon containing 50% water, 1.2 g), and 1.6 g of magnesium oxide (2 equivalents based upon 4-chloro-3,5-dinitrobenzotrifluoride). After purging with nitrogen, hydrogen was charged periodically in the reaction bottle to maintain its pressure at 40-50 psig. The reaction temperature began at approximately 21° C. and began to rise as soon as the agitation began. In 7 minutes, the temperature rose to 80° C. and was held at 80° C. for 1 hour. The reaction mixture was then allowed to cool to room temperature over approximately 25 minutes. After the reaction, the analysis of the mixture by gas chromatography showed the presence of 5.91 g of 3,5-diaminobenzotrifluoride and 0.44 g of 4-chloro-3,5-diaminobenzotrifluoride. The yield of 3,5-diaminobenzotrifluoride was 91% based upon starting material.

Comparative Example 6

A solution of 10 g of 4-chloro-3,5-dinitrobenzotrifluoride in 1-propanol (120 mL) was charged in a Parr hydrogenator bottle and mixed with a carbon supported palladium catalyst (5% Pd on carbon containing 50% water, 1.2 g), and 1.6 g of magnesium oxide (2 equivalents based upon 4-chloro-3,5-dinitrobenzotrifluoride). After purging with nitrogen, hydrogen was charged periodically in the reaction bottle to maintain its pressure at 40–50 psig. The reaction temperature began at approximately 27° C. and began to rise as soon as the agitation began. In 8 minutes, the temperature rose to 78° C. and was held at 80° C. for 1 hour. The reaction mixture was then allowed to cool to room temperature over approximately 37 minutes. After the reaction, the analysis of the mixture by gas chromatography showed the presence of 5.41 g of 3,5-diaminobenzotrifluoride and 0.88 g of 4-chloro-3,5-diaminobenzotrifluoride. The yield of 3,5-diaminobenzotrifluoride was 83% based upon starting material.

Comparative Example 7

A solution of 10 g of 4-chloro-3,5-dinitrobenzotrifluoride in ethyl acetate (100 mL) was charged in a Parr hydrogenator bottle and mixed with a carbon supported palladium catalyst (5% Pd on carbon containing 50% water, 1.2 g), and 3.0 g (4 equivalents based upon the 4-chloro-3,5-dinitrobenzotrifluoride) of magnesium oxide. After purging with nitrogen, hydrogen was charged periodically in the reaction bottle to maintain its pressure at 40–50 psig. The reaction temperature began at approximately 22° C. and began to rise as soon as the agitation began. In 17 minutes, the temperature rose to 80° C. and was held at 80° C. for 30 minutes. The reaction mixture was then allowed to cool to room temperature over approximately 43 minutes. After the reaction, the analysis of the mixture by gas chromatography showed the presence of 3.90 g of 3,5-diaminobenzotrifluoride and 2.62 g of 4-chloro-3,5-diaminobenzotrifluoride. The yield of 3,5-diaminobenzotrifluoride was 60% based upon starting material.

Comparative Example 8

A solution of 10 g of 4-chloro-3,5-dinitrobenzotrifluoride in isopropyl alcohol (100 mL) was charged in a Parr hydrogenator bottle and mixed with a carbon supported palladium catalyst (5% Pd on carbon containing 50% water, 1.2 g), and 3.0 g (4 equivalents based upon the 4-chloro-3,5-dinitrobenzotrifluoride) of magnesium oxide. After purging with nitrogen, hydrogen was charged periodically in the reaction bottle to maintain its pressure at 40–50 psig. The reaction temperature began at approximately 30° C. and began to rise as soon as the agitation began. In 15 minutes, the temperature rose to 80° C. and was held at 80° C. for 43 minutes. The reaction mixture was then allowed to cool to room temperature over approximately 57 minutes. After the reaction, the analysis of the mixture by gas chromatography showed the presence of 4.02 g of 3,5-diaminobenzotrifluoride and 2.53 g of 4-chloro-3,5-diaminobenzotrifluoride. The yield of 3,5-diaminobenzotrifluoride was 62% based upon starting material.

Comparative Example 9

The hydrogenation was run in methanol without any base. A solution of 4-chloro-3,5-dinitrobenzotrifluoride (10 g) in methanol (100 mL) was charged in a Parr hydrogenator bottle and mixed with a carbon supported palladium catalyst (5% Pd on carbon containing 50% water, 1.2 g wet weight). After purging with nitrogen, hydrogen was charged periodically in the reaction bottle to maintain its pressure at 40–50 psig. The reaction began at 20° C. and began to rise as soon as agitation began. The temperature rose to 76° C. in seven minutes. The reaction mixture was held at 80° C. for two hours and then allowed to cool to room temperature over a period of 30 minutes. After the reaction, analysis of the reaction mixture by gas chromatography showed formation of 2.85 g of 3,5-diaminobenzotrifluoride and 0.76 g of 4-chloro-3,5-diaminobenzotrifluoride. The yield of 3,5-diaminobenzotrifluoride based upon starting material was 44% which indicates that there is an appreciable amount of product not detected by gas chromatography.

We claim:

1. A process for the preparation of 3,5-diaminobenzotrifluoride which comprises treating 4-chloro-3,5-dinitrobenzotrifluoride, in a methanol solvent, with hydrogen gas in the presence of magnesium oxide and in the presence of a catalyst which comprises palladium on a carbon support.

2. A process according to claim 1 in which the catalyst is 5% palladium on carbon.

3. A process according to claim 2 in which the catalyst is present at a level of 4 g (dry weight) per 100 g of 4-chloro-3,5-dinitrobenzotrifluoride.

4. A process according to claim 3 run at a temperature up to 90° C.

5. A process according to claim 3 run at a temperature up to 125° C.

6. A process according to claim 2 in which the catalyst is present at a level of 6 g (dry weight) per 100 g of 4-chloro3,5-dinitrobenzotrifluoride.

7. A process according to claim 6 run at a temperature up to 90° C.

8. A process according to claim 6 run at a temperature up to 125° C.

9. A process according to claim 2 in which the catalyst is present at a level of 1 g (dry weight) per 100 g of 4-chloro3,5-dinitrobenzotrifluoride.

10. A process according to claim 9 run at a temperature up to 90° C.

11. A process according to claim 9 run at a temperature up to 125° C.

12. A process according to claim 2 in which the catalyst is present at a level of 0.5 g (dry weight) per 100 g of 4-chloro-3,5-dinitrobenzotrifluoride.

13. A process according to claim 12 run at a temperature up to 90° C.

14. A process according to claim 12 run at a temperature up to 125° C.

15. A process according to claim 1 including the additional last step of evaporating said methanol.

16. A process according to claim 1 wherein the concentration of said 4-chloro-3,5-dinitrobenzotrifluoride in said methanol is up to 0.17 g/mL.

17. A method of converting at least 87% of 4-chloro-3,5-dinitrobenzotrifluoride into 3,5-diaminobenzotrifluoride and into less than 0.5% 4-chloro-3,5-diaminobenzotrifluoride comprising (A) preparing a mixture of a solution of up to 0.17 g/mL 4-chloro-3,5-dinitrobenzotrifluoride in methanol in the presence of hydrogen, a palladium or carbon catalyst, and at least one equivalent of magnesium oxide; and (B) heating said mixture to a temperature between room temperature and 125° C.

18. A method according to claim 17 including the additional last step of evaporating said solvent.

19. A process according to claim 17 in which the catalyst is 5% palladium on carbon.

20. A method according to claim 17 wherein concentration of said catalyst is 4 to 6 g (dry weight) per 100 g of 4-chloro-3,5-dinitrobenzotrifluoride.

* * * * *